United States Patent
Sivan et al.

(10) Patent No.: US 6,569,688 B2
(45) Date of Patent: *May 27, 2003

(54) INTRAVASCULAR APPARATUS METHOD

(75) Inventors: Sarit Sivan, Zichron Yaakov (IL); Uri Dinnar, Haifa (IL); Noah Lotan, Haifa (IL)

(73) Assignee: Technion Research & Development Foundation Ltd., Haifa (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/486,362

(22) PCT Filed: Aug. 13, 1998

(86) PCT No.: PCT/US98/16823
§ 371 (c)(1),
(2), (4) Date: Feb. 28, 2000

(87) PCT Pub. No.: WO99/09912
PCT Pub. Date: Mar. 4, 1999

(65) Prior Publication Data
US 2002/0182750 A1 Dec. 5, 2002

Related U.S. Application Data

(62) Division of application No. 08/917,609, filed on Aug. 26, 1997, now abandoned.

(51) Int. Cl.⁷ .............................................. G01N 33/543
(52) U.S. Cl. ................... 436/518; 435/4; 435/287.9; 424/1.29; 424/9.33; 422/57; 436/524
(58) Field of Search ................. 422/57, 294; 536/24.5; 435/174, 4, 176, 7.1, 180, 182, 188.5; 424/146.1, 94.1, 1.29, 9.322, 410; 558/299; 623/1, 1.12; 606/194, 195; 436/518, 524

(56) References Cited

U.S. PATENT DOCUMENTS

| | | | |
|---|---|---|---|
| 5,314,688 A | | 5/1994 | Kauffman et al. |
| 5,428,070 A | * | 6/1995 | Cooke et al. ............... 514/557 |
| 5,429,634 A | | 7/1995 | Narciso, Jr. |
| 5,441,515 A | * | 8/1995 | Khosravi et al. ........... 606/194 |
| 5,500,013 A | | 3/1996 | Buscemi et al. |
| 5,512,291 A | | 4/1996 | Li |
| 5,514,379 A | | 5/1996 | Weissleder et al. |
| 5,578,075 A | * | 11/1996 | Dayton et al. .............. 424/422 |
| 5,833,651 A | * | 11/1998 | Donovan et al. ........... 604/509 |
| 5,925,353 A | * | 7/1999 | Mosseri et al. ........... 424/178.1 |
| 6,143,037 A | * | 11/2000 | Goldstein et al. ........... 623/1.15 |
| 6,180,824 B1 | * | 1/2001 | Stamler et al. ............. 562/507 |

* cited by examiner

*Primary Examiner*—Long V. Le
*Assistant Examiner*—Gary Counts
(74) *Attorney, Agent, or Firm*—G. E. Ehrlich Ltd.

(57) ABSTRACT

Intravascular apparatus and method for locally treating a patient's blood vessel, are provided. The apparatus includes an implanted carrier (2) for insertion into the vessel; and a biologically active agent (8) immobilized to the carrier (2), said biologically active agent (8) reacting with a first substance to produce a second substance. The second substance is preferably a therapeutic agent, such as nitric oxide, for locally treating the vessel. The biologically active agent (8) is preferably an enzyme such as nitrogen oxide synthase, and the first substance is preferably arginine introduced to the patient's body as part of a diet. According to another embodiment, the biologically active agent (8) is a catalytic antibody and the first substance is a prodrug. Alternatively, the biologically active agent (8) is a ribozyme. The method includes introducing into a patient's vessel an implantable carrier including a biologically active agent immobilized thereto, and reacting the biologically active agent with a first substance to locally produce a second substance.

31 Claims, 1 Drawing Sheet

INTRAVASCULAR APPARATUS METHOD

This application is a 371 of PCT/US98/16823 which is a divisional of Ser. No. 08/917,609 filed Aug. 26, 1997, now abandoned.

FIELD AND BACKGROUND OF THE INVENTION

The present invention relates to intravascular apparatus and method for preventing restenosis of a patient's blood vessel by locally treating a portion of the vessel. More particularly, the present invention relates to an implantable carrier for insertion into a blood vessel, the carrier including biologically active agents immobilized thereto for selectively reacting with a supplied substance to locally produce a therapeutic agent. Preferably, the biologically active materials are enzymes reacting with a substrate introduced to the patient's body as part of his diet to produce a therapeutic agent having cell proliferation inhibiting activity.

It is well known that excessive proliferation of vascular smooth muscle cells contributes to restenosis and reocclusion of coronary arteries following procedures such as percutaneous transluminal coronary angioplasty (PTCA), artherectomy, laser angioplasty and arterial bypass graft.

Various attempts have been made to provide intravascular implants for preventing restenosis and reocclusion of blood vessels, the implants incorporating therapeutic agents such as cell proliferation inhibiting factors for locally treating the vessel. Examples are disclosed in U.S. Pat. Nos. 5,314,688, 5,514,379, 5,512,291, 5,500,013 and 5,429,634.

However, most of these disclosures provide intravascular devices loaded with biologically active agents such as drugs, drug-producing enzymes or drug-producing cells, the biologically active agents being slowly released from the device to the circulating blood.

The maximal amount of such biologically active agents incorporated into the intravascular device is limited by the physical dimensions of the device, thereby substantially limiting the effective period of treatment. When treating restenosis caused by progressive cell proliferation, it is necessary to supply therapeutic agents for at least several months in order to produce a substantial therapeutic effect. The prior art fails to provide an effective therapeutic treatment for such an extended period of time.

Further, the prior art fails to provide an efficient method for controlling the concentration of the therapeutic agent at the site of treatment, or alternatively to produce trends in such concentration.

Further, by using biologically active agents such as drug-producing enzymes which are slowly released into the blood circulation, the prior art provides a systemic rather than local treatment. Once these drug-producing enzymes are released into the circulation, their concentration at the site of treatment is significantly diluted and accordingly, their activity is substantially diminished.

Further, because of the systemic nature of such method of therapy, it does not enable to use therapeutic agents having a substantially short life time, since once such therapeutic agents are in the blood circulation, they are likely to loose their activity before having the chance to reach the site of treatment.

Further, none of the above disclosures provides apparatus and method wherein a therapeutic agent is locally and controllably produced within the patient's blood vessel upon provision of an appropriate diet.

Further, none of the above disclosures provides apparatus and method wherein the therapeutic agent is produced by means of biologically active agents such as enzymes immobilized to the apparatus.

There is thus a widely recognized need for, and it would be highly advantageous to have, intravascular apparatus and method which provide an effective local treatment of a patient's vessel for an extended period of time.

It would be further advantageous to have such apparatus and method wherein the amount of therapeutic agent provided by such apparatus is not limited by its physical dimensions.

It would be further advantageous to have such apparatus and method which enable to control the concentration of therapeutic agent at the site of treatment, and to produce trends in such concentration.

Further, it would be advantageous to have such apparatus and method which enable to use therapeutic agents having substantially short life-time in the systemic circulation.

Further, it would be advantageous to have such apparatus and method wherein a therapeutic agent is locally and controllably produced within the patient's blood vessel by providing an appropriate diet.

Further, it would be advantageous to have such apparatus and method wherein the therapeutic agent is produced by means of biologically active agents such as enzymes immobilized to the apparatus.

SUMMARY OF THE INVENTION

According to the present invention there is provided an intravascular apparatus for locally treating a patient's blood vessel, comprising: (a) an implantable carrier for insertion into the vessel; and (b) a biologically active agent immobilized to the carrier, the biologically active agent reacting with a first substance to produce a second substance. The second substance is preferably a therapeutic agent such as nitric oxide for locally treating the vessel. The biologically active agent is preferably an enzyme such as nitrogen oxide synthase. Preferably, the first substance is arginine and is introduced to the patient's body as part of a diet. Alternatively, the biologically active agent is a catalytic antibody specifically tailored to react with a specific substrate to give a desired therapeutic agent. Alternatively, the biologically active agent is a ribozyme.

According to still further features in the described preferred embodiments the biologically active agent is chemically attached to the implantable carrier. Alternatively, the biologically active agent is entrapped within a polymeric network covering the implantable carrier.

According to another embodiment the first substance is an undesirable agent at the site of treatment. The biologically active agent may be an enzyme having anti thrombogenic activity, such as Tissue Plasminogen Activator. Alternatively, the biologically active agent is a catalytic antibody. Alternatively, the biologically active agent is a ribozyme.

According to the present invention there is further provided a method for locally treating a patient's vessel, comprising: (a) introducing into a patient's vessel an implantable carrier including a biologically active agent immobilized thereto; and (b) reacting the biologically active agent with a first substance to locally produce a second substance. Preferably, the method further comprises introducing the first substance to the patient's body. Further, the method preferably comprises controlling the concentration of the second substance by changing the concentration of the first substance introduced to the patient's body. Preferably, the first substance is introduced to the patient's body as part of a diet.

The present invention successfully addresses the shortcomings of the presently known configurations by providing an intravascular apparatus and method which provide an effective local treatment of a patient's vessel for an extended period of time. Further, the present invention addresses the shortcomings of the presently known configurations by providing an intravascular apparatus and method wherein the total amount of therapeutic agent provided by such apparatus is not limited by its physical dimensions. Further, the present invention addresses the shortcomings of the presently known configurations by providing an intravascular apparatus and method which enable to control the concentration of therapeutic agent at the site of treatment, and to produce trends in such concentration. Further, the present invention addresses the shortcomings of the presently known configurations by providing an intravascular apparatus and method which enable to use therapeutic agents having substantially short life-time in the systemic circulation.

The present invention discloses a novel intravascular apparatus and method wherein a therapeutic agent is locally and controllably produced within the patient's blood vessel upon introduction of an appropriate diet. Further, the present invention discloses a novel intravascular apparatus and method wherein the therapeutic agent is produced by means of biologically active agents such as enzymes immobilized to the apparatus.

BRIEF DESCRIPTION OF THE DRAWINGS

The invention is herein described, by way of example only, with reference to the accompanying drawing, wherein.

DESCRIPTION OF THE PREFERRED EMBODIMENTS

Figure 1:
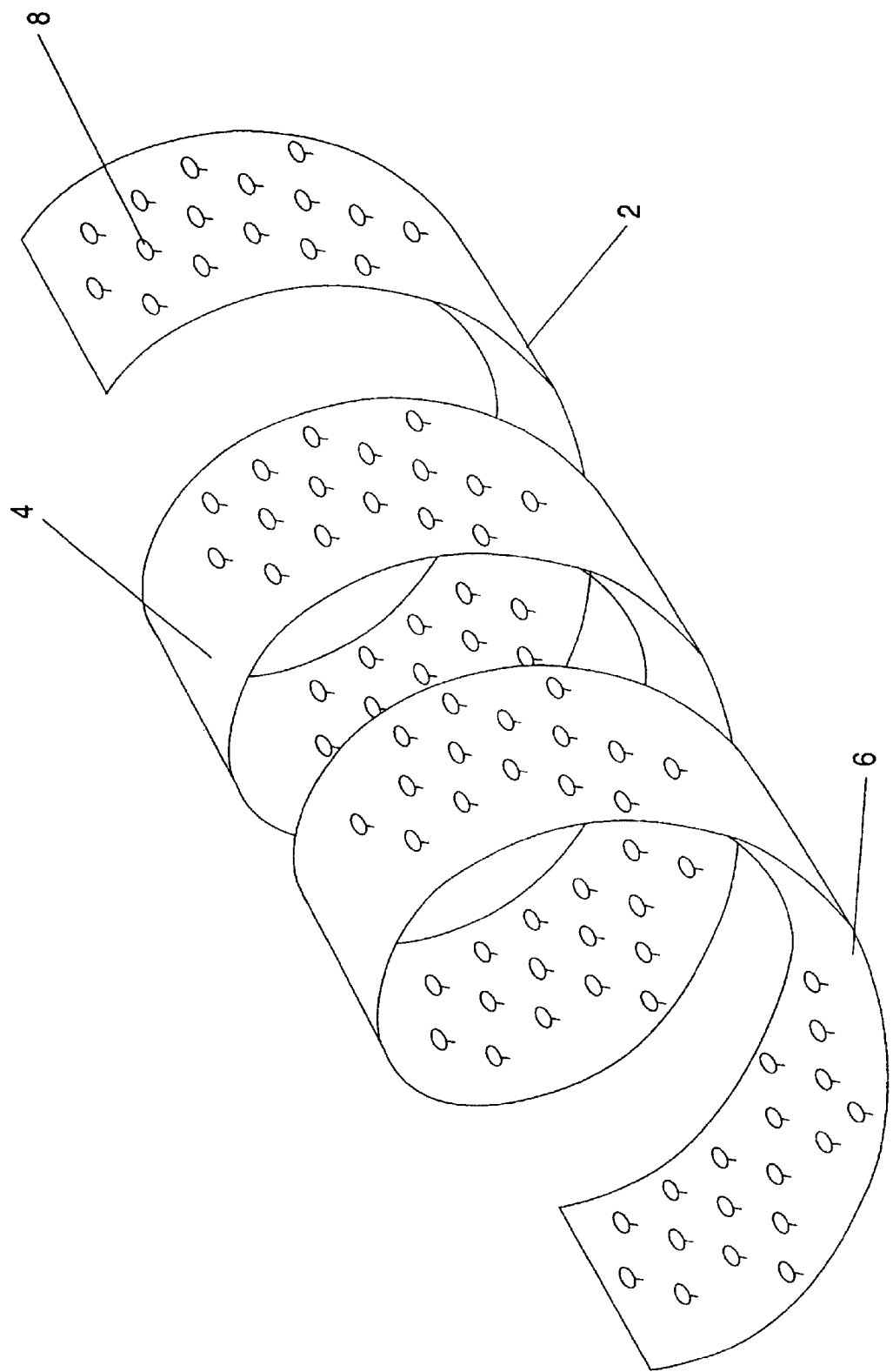
FIG. 1 is a schematic illustration of a preferred embodiment of an intravascular apparatus according to the present invention.

The present invention is of intravascular apparatus and method for preventing restenosis of a patient's vessel by locally treating a portion of the vessel.

The principles and operation of apparatus and method according to the present invention may be better understood with reference to the drawing and the accompanying description.

FIG. 1 illustrates a preferred embodiment of intravascular apparatus according to the present invention. As shown in the figure, the intravascular apparatus comprises an implantable carrier such as a conventional stent 2 for insertion into a patient's blood vessel, the stent including biologically active agents 8 such as enzymes attached thereto. Biologically active agents 8 are preferably immobilized to outer surface 4 and inner surface 6 of stent 2.

Preferably, stent 2 has a shape of a spiral. Alternatively, stent 2 has a shape of a solid cylinder, a perforated cylinder, a mesh, or any other shape.

Stent 2 is preferably made of metal such as platinum, gold, titanium, and nickel. Alternatively, stent 2 may be made of metal alloys such as stainless steel and nickel-titanium alloy (nitinol). Alternatively stent 2 may be made of non-degradable polymers or copolymers such as polyethylene, polypropylene, poly(acrylic acid), poly (ethylene oxide), and poly (ethylene oxide-co-propylene oxide).

Preferably, stent 2 is coated with a layer of a crosslinked polymer, or alternatively protein, so as to confer biocompatibility characteristics to the stent.

Preferably, biologically active agent 8 reacts with a supplied substance to produce a predetermined therapeutic agent. Preferably, biologically active agent 8 is an enzyme and the supplied substance is a specific substrate introduced into the patient's body as part of a diet.

According to a preferred embodiment of the present invention, the enzyme is nitrogen oxide synthase, and the substrate is the natural amino acid arginine which is easily introduced into the patient's blood circulation as part of an appropriate diet. The products of such enzymatic reaction are citrulline and nitric oxide (NO), the latter having a cell proliferation inhibiting activity.

Thus, according to the present invention, the therapeutic agent is locally produced upon introduction of an appropriate substance. The substance may be continuously introduced into the patient's body as long as the treatment is needed. Therefore, the maximal amount of therapeutic agent which may be supplied for treating the blood vessel is not limited by the physical dimensions of the apparatus.

The life time of the apparatus is however limited by the life time of the biologically active agent. For example, when the biologically active agent is an enzyme, the biological activity of the enzyme lasts for at least several months, which is the time needed for inducing a substantial therapeutic effect.

A treatment according to the present invention may be terminated at any time by using inhibitors for blocking the activity of biologically active agent 8 or by dissociating the bonds between biologically active agent 8 and stent 2.

According to the present invention the concentration of the therapeutic agent supplied at the site of treatment is controllable, simply by controlling the concentration of the substance introduced into the patient body. Further, the present invention allows to produce trends in the concentration of the therapeutic agent.

For example, when the therapeutic agent is nitric oxide produced by reacting nitrogen oxide synthase and arginine, the amount of nitric oxide at the site of treatment depends mainly on the concentration of arginine circulating in the blood. The latter can be altered as required by the physiological condition of the patient and by the nitric oxide concentration needed for an effective therapy. Thus, when alteration of the nitric oxide concentration are called for by the therapeutic requirements, these may be achieved by merely altering the amount and concentration of arginine supplied to the patient as part of his diet.

Further, the present invention enables to use therapeutic agents having a substantially short life time, since the therapeutic agent is locally produced at the site of treatment.

For example, the life time of nitric oxide in blood circulation is very short (of the order of magnitude of seconds). Once in the blood circulation, nitric oxide is converted into nitrite and nitrate. However, since nitric oxide is locally produced at the site of treatment, it has the opportunity to induce the required therapeutic effect before being washed away by the blood stream and converted into the inactive species nitrite and nitrate.

According to the present invention, biologically active agents 8 may be chemically attached onto the surface of stent 2, or alternatively may be entrapped within a polymeric hydrogel network that covers the stent.

When using enzymes and a metallic stent, the enzymes may be chemically attached to the stent by means of the following procedure: (i) treatment of the stent with 3-aminopropyl thriethoxysilane; (ii) treatment with glutaraldehyde; and (iii) coupling of the enzyme.

Alternatively, the enzymes may be entrapped within a polymeric hydrogel network covering the stent by means of the following procedure: (i) treatment of the stent with 3-acryloxypropyl trimethoxysilane; and (ii) photopolymerization of a mixture of the enzyme and alpha, omega-diacryloyl polyethylene glycol.

According to another preferred embodiment, biologically active agent 8 is a catalytic antibody which reacts with the supplied substrate (a prodrug) to give a therapeutic agent.

By using a catalytic antibody specifically tailored to react with a specific substance (Molecular Biology and Biotechnology, Robert M. Myers Ed., VCH 1995), such embodiment enables to locally produce any desired therapeutic agent.

Alternatively, biologically active agent 8 is a catalytic RNA molecule (ribozyme). The ribozyme may be specifically engineered (Molecular Biology and Biotechnology, Robert M. Myers Ed., VCH 1995) so as to specifically cleave a certain substance. The ribozyme may be a ribonucleoprotein enzyme (RNP).

According to yet another preferred embodiment, biologically active agent 8 reacts with a substance having an undesirable effect at the site of treatment to produce an agent having a neutral effect.

Preferably, biologically active agent 8 is an enzyme such as superoxide dismutase which reacts with superoxide, the latter being an undesirable substance at the site of treatment when using nitric oxide as a therapeutic agent. Superoxide reacts with nitric oxide to give peroxynitrite, thereby substantially reducing the concentration of nitric oxide at the site of treatment, thereby reducing the therapeutic effect.

Alternatively, biologically active agent 8 is an enzyme such as Tissue Plasminogen Activator which is a platelet anti-aggregation factor. Thus, incorporation of such an enzyme into stent 2 is likely to cancel eventual thrombogenicity of the apparatus and the blood vessel.

Alternatively, biologically active agent 8 is a catalytic antibody which reacts with a substrate having an undesirable effect at the site of treatment to produce an agent having a neutral effect.

By using a catalytic antibody specifically tailored to react with a specific substance (Molecular Biology and Biotechnology, Robert M. Myers Ed., VCH 1995), such embodiment enables to remove any substance having an undesirable effect at the site of treatment. Further, such embodiment enables to remove any substance having a systemic undesirable effect.

Alternatively, biologically active agent 8 is a catalytic RNA molecule (ribozyme). The ribozyme may be specifically engineered (Molecular Biology and Biotechnology, Robert M. Myers Ed., VCH 1995) so as to specifically cleave a targeted substance. The targeted substance is preferably a DNA or RNA molecule having an undesirable biological effect. The ribozyme may be a ribonucleoprotein enzyme (RNP).

According to further features of the preferred embodiments, materials having anti-thrombogenic and anti-platelet aggregation activity may be incorporated into stent 2. Such materials may include, for example, heparin, low molecular weight heparin fragments, and sulfated polysaccharides. Such anti thrombogenic materials may be chemically bound to the stent or to a polymeric hydrogel layer covering the stent. Alternatively, such materials may be entrapped within a polymeric hydrogel layer covering the stent.

Other preferred materials which may be incorporated into stent 2 include drugs such as Aspirin or Ticlopidine, the drugs being slowly releasable from stent 2 during the first few days of implantation so as to reduce thrombus formation.

Further, biocompatibility inducing factors such as polyethylene glycol (PEG) chains may be chemically bound to stent 2 for conferring good biocompatibility characteristics to the stent.

A dense array of such PEG chains also slows down the outward diffusion of the nitric oxide produced in the apparatus, thereby allowing to achieve a high local concentration of nitric oxide at the site of treatment. Further, PEG chains prevent the deposition of cellular elements from the blood.

While the invention has been described with respect to a limited number of embodiments, it will be appreciated that many variations, modifications and other applications of the invention may be made.

What is claimed is:

1. An intravascular apparatus for locally treating a patient's vessel, comprising:
   (a) an implantable carrier for insertion into the vessel; and
   (b) an enzyme covalently immobilized to said carrier,
   while being covalently immobilized to said implantable carrier, said enzyme being continuously reactable with a first substance to locally produce a second substance.

2. The apparatus of claim 1, wherein said second substance is a therapeutic agent for locally treating the vessel.

3. The apparatus of claim 2, wherein said therapeutic agent is nitric oxide.

4. The apparatus of claim 1, wherein said enzyme is nitrogen oxide synthase.

5. The apparatus of claim 1, wherein said enzyme is superoxide dismutase.

6. The apparatus of claim 1, wherein said enzyme is Tissue Plasminogen Activator.

7. The apparatus of claim 1, wherein said first substance is introduced to the patient's body as part of a diet.

8. The apparatus of claim 1, wherein said first substance is arginine.

9. The apparatus of claim 1, wherein said first substance is superoxide.

10. The apparatus of claim 1, wherein said enzyme is a catalytic antibody.

11. The apparatus of claim 1, wherein said enzyme is a ribozyme.

12. The apparatus of claim 1, wherein said carrier is a stent.

13. The apparatus of claim 1, wherein said enzyme is entrapped within a polymeric network covering said implantable carrier.

14. An intravascular apparatus for locally treating a patient's vessel, comprising:
   (a) a stent for insertion into die vessel; and
   (b) an enzyme covalently immobilized to said stent,
   while being covalently immobilized to said stent, said enzyme being continuously reactable with a first substance to locally produce a second substance.

15. The apparatus of claim 14, wherein said first substance is introduced to the patient's body as part of his diet.

16. The apparatus of claim 14, wherein said enzyme is a catalytic antibody.

17. The apparatus of claim 14, wherein said enzyme is a ribozyme.

18. A method for locally h-eating a patient's vessel, comprising:
   (a) introducing into a patient's vessel an implantable carrier including an enzyme covalently immobilized thereto; and
   (b) while being covalently immobilized to said implantable carrier, reacting said immobilized enzyme with a fast substance to locally produce a second substance.

19. The method of claim 18, further comprising introducing said first substance to said patient's body.

20. The method of claim 18, further comprising controlling the concentration of said second substance by changing the concentration of said first substance introduced to the patient's body.

21. The method of claim 18, wherein said first substance is introduced to the patient's body as part of a diet.

22. The method of claim 21, further comprising controlling the concentration of said second substance by changing said diet.

23. The method of claim 18, wherein said second substance is a therapeutic agent for locally treating the vessel.

24. The method of claim 23, wherein said therapeutic agent is nitric oxide.

25. The method of claim 18, wherein said enzyme is nitrogen oxide synthase.

26. The method of claim 18, wherein said enzyme is superoxide dismutase.

27. The method of claim 18, wherein said enzyme is Tissue Plasminogen Activator.

28. The method of claim 18, wherein said first substance is arginine.

29. The method of claim 18, wherein said first substance is superoxide.

30. The method of claim 18, wherein said enzyme is a catalytic antibody.

31. The method of claim 18, wherein said enzyme is a ribozyme.

\* \* \* \* \*

UNITED STATES PATENT AND TRADEMARK OFFICE
CERTIFICATE OF CORRECTION

PATENT NO. : 6,569,688 B2
DATED : May 27, 2003
INVENTOR(S) : Sarit Sivan et al.

It is certified that error appears in the above-identified patent and that said Letters Patent is hereby corrected as shown below:

Title page, Item [54] and Column 1, line 1,
Title, add -- AND -- after "APPARATUS".

Column 7,
Line 3, replace "h-eating" with -- treating --.
Line 10, replace "fast" with -- first --.

Signed and Sealed this

Fourteenth Day of February, 2006

JON W. DUDAS
*Director of the United States Patent and Trademark Office*